(12) United States Patent
Gong et al.

(10) Patent No.: US 11,571,670 B2
(45) Date of Patent: Feb. 7, 2023

(54) MATERIAL INTAKE DEVICE AND UREA PREPARATION MACHINE WITH MATERIAL INTAKE DEVICE

(71) Applicants: ZHUHAI GREE INTELLIGENT EQUIPMENT CO., LTD, Zhuhai (CN); GREE ELECTRIC APPLIANCES, INC. OF ZHUHAI, Zhuhai (CN)

(72) Inventors: Ke Gong, Zhuhai (CN); Xiufeng Zhang, Zhuhai (CN)

(73) Assignees: ZHUHAI GREE INTELLIGENT EQUIPMENT CO., LTD, Zhuhai (CN); GREE ELECTRIC APPLIANCES, INC. OF ZHUHAI, Zhuhai (CN)

( * ) Notice: Subject to any disclaimer, the term of this patent is extended or adjusted under 35 U.S.C. 154(b) by 1002 days.

(21) Appl. No.: 16/332,554

(22) PCT Filed: Nov. 28, 2017

(86) PCT No.: PCT/CN2017/113339
§ 371 (c)(1),
(2) Date: Mar. 12, 2019

(87) PCT Pub. No.: WO2018/107962
PCT Pub. Date: Jun. 21, 2018

(65) Prior Publication Data
US 2021/0283562 A1    Sep. 16, 2021

(30) Foreign Application Priority Data
Dec. 13, 2016 (CN) .......................... 201611152474.3

(51) Int. Cl.
*B01F 35/71* (2022.01)
*B01F 35/00* (2022.01)

(52) U.S. Cl.
CPC .............. *B01F 35/71* (2022.01); *B01F 35/55* (2022.01)

(58) Field of Classification Search
CPC .................................. B01F 35/55; B01F 35/71
(Continued)

(56) References Cited

U.S. PATENT DOCUMENTS 4,135,643 A    1/1979  Mieschke

FOREIGN PATENT DOCUMENTS

| CN | 201735264 U | 2/2011 |
| CN | 202590724 U | 12/2012 |

(Continued)

OTHER PUBLICATIONS

The World Intellectual Property Organization (WIPO) International Search Report for PCT/CN2017/113339 dated Mar. 2, 2018 6 Pages.

*Primary Examiner* — Marc C Howell
(74) *Attorney, Agent, or Firm* — Anova Law Group, PLLC (57) ABSTRACT

Some embodiments of the present disclosure provide a material intake device and a urea preparation machine. The material intake device includes a housing, an inlet port is provided at a first end of the housing, and an outlet port is provided at a second end of the housing, and the housing is further provided with an exhaust port used for exhausting an air in the housing; a separation plate is provided within the housing to isolate the inlet port from the exhaust port, an air inlet duct and an exhaust ductexhaust duct are formed respectively between the separation plate and sidewalls of the housing, the exhaust port is communicated with the exhaust ductexhaust duct, and an overflow port connecting (Continued)

the air inlet duct to the exhaust ductexhaust duct is provided between a bottom of the separation plate and the sidewalls of the housing.

20 Claims, 7 Drawing Sheets

(58) Field of Classification Search
USPC .......................................................... 422/240
See application file for complete search history.

(56) References Cited

FOREIGN PATENT DOCUMENTS

| | | |
|---|---|---|
| CN | 204182373 U | 3/2015 |
| CN | 204973750 U | 1/2016 |
| CN | 105536635 A | 5/2016 |
| CN | 106582336 A | 4/2017 |
| CN | 206366365 U | 8/2017 |

MATERIAL INTAKE DEVICE AND UREA PREPARATION MACHINE WITH MATERIAL INTAKE DEVICE

CROSS REFERENCE TO RELATED APPLICATIONS

This application is a national phase entry under 35 U.S.C § 371 of International Application No. PCT/CN2017/113339, filed on Nov. 28, 2017, which claims priority to Chinese Patent Application No. 201611152474.3, filed on Dec. 13, 2016, the entire content of all of which are hereby incorporated by their reference.

TECHNICAL FIELD

The present disclosure relates to a technical field of urea processing devices and, in particular, to a material intake device and a urea preparation machine with the material intake device.

BACKGROUND

A heating device in a urea preparation machine in a related art is generally provided in a stirring tank, or provided in an ultrapure water tank to heat water entering the stirring tank in the urea preparation machine and prepare urea solution. Heating modes in the related art are limited, in the case of using a lot of the urea solution, the heating modes in the related art which are used for heating the water may not satisfy user requirements, and production efficiency of the urea solution is reduced. Besides, a material intake device used of the urea preparation machine in the related art is provided with a filtering screen at a feeding port, urea particles entering a housing are easily blocked by using a mode of the filter screen, so a problem that the feeding port is easily blocked is caused.

SUMMARY

Some embodiments of the present disclosure mainly aim to provide a material intake device and a urea preparation machine with the same, and solve a problem in a related art that a material intake port is easily blocked.

In order to achieve the above purpose, some embodiments of the present disclosure provide a material intake device. The material intake device includes a housing, wherein a inlet port is provided at a first end of the housing, and an outlet port is provided at a second end of the housing, and the housing is further provided with an exhaust port used for exhausting air in the housing; a separation plate, which is provided within the housing to isolate the inlet port from the exhaust port, an air inlet duct and an exhaust duct are formed respectively between the separation plate and sidewalls of the housing, and the exhaust port is communicated with the exhaust duct, and an overflow port connecting the air inlet duct to the exhaust duct is provided between a bottom of the separation plate and the sidewalls of the housing.

In an exemplary embodiment the separation plate includes a first plate segment, the first plate segment is provided along a vertical direction, a first end of the first plate segment is connected to the housing, the inlet port and the exhaust port are provided at two opposite sides of the first plate segment; a second plate segment, wherein the second plate segment is connected to a second end of the first plate segment with an included angle and the second plate segment is provided away from the exhaust port.

In an exemplary embodiment, the included angle between the second plate segment and the second end of the first plate segment is a right angle.

In an exemplary embodiment, the material intake device includes a suction portion, the suction portion is provided with an inlet and an outlet, the outlet is communicated with a feeding port, and the inlet is used for sucking urea so as to convey urea into the housing.

In an exemplary embodiment, the material intake device includes a material striking portion, the material striking portion is rotatably provided in the housing so as to remove urea attached to the housing.

In an exemplary embodiment, the material striking portion includes a connecting rod, wherein the connecting rod is rotatably provided at the feeding port, a first end of the connecting rod is extended towards an interior of the housing, a second end of the connecting rod is extended towards an exterior of the housing; a rolling plate, wherein the rolling plate is connected to the first end of the connecting rod, the rolling plate is extended along the side wall of the housing, the connecting rod drives the rolling plate to rotate along a circumferential direction of the housing.

In an exemplary embodiment, the material striking portion further includes a handle, where the handle is provided on the second end of the connecting rod.

In an exemplary embodiment, the material striking portion includes a material blocking plate, where the material blocking plate is provided in the housing and positioned below the rolling plate.

In an exemplary embodiment, the material intake device includes an inlet pipe segment, where one end of the inlet pipe segment is communicated with a cavity of the housing, the side wall of the inlet pipe segment is provided with the feeding port, the other end of the inlet pipe segment is a free end and is closed, a part of the connecting rod is positioned in the inlet pipe segment and the connecting rod and the inlet pipe segment are coaxially provided.

In an exemplary embodiment, the housing is further provided with a water inlet.

Some embodiments of the present disclosure provide a urea preparation machine. The urea preparation machine includes a material intake device, the material intake device is the above material intake device.

The embodiment of the present disclosure is applied, the material intake device includes a housing, an inlet port is provided at a first end of the housing, and an outlet port is provided at a second end of the housing, and the housing is further provided with an exhaust port used for exhausting air in the housing; a separation plate is provided within the housing to isolate the inlet port from the exhaust port, an air inlet duct and an exhaust duct are provided respectively between the separation plate and sidewalls of the housing, the exhaust port is communicated with the exhaust duct, an overflow port connecting the air inlet duct to the exhaust duct is provided between a bottom of the separation plate and the sidewalls of the housing. Disposing the separation plate between the inlet port and the exhaust port to separate the inlet port and the exhaust port can effectively prevent urea particles from discharging from the exhaust port resulting in waste thereof when intaking the urea particles from the inlet port and exhausting the air in the material intake device, and at the same time can effectively prevent the urea particles from blocking at the material feeding port so as to affect the production of urea solutions.

BRIEF DESCRIPTION OF THE DRAWINGS

The accompanying drawings, which constitute a part of this application, are used to provide a further understanding of the disclosure, and the exemplary embodiments of the disclosure and the description thereof are used to explain the disclosure, but do not constitute improper limitations to the disclosure. In the drawings.

Herein, above drawings include the following reference characters:

10: cabinet; 20: stirring tank; 21: material intake device; 211: inlet port; 212: exhaust port; 213: separation plate; 214: water inlet; 2131: first plate segment; 2132: second plate segment; 22: suction portion; 23: material striking portion; 231: connecting rod, 232: rolling plate; 233: handle, 234: material blocking plate; 30: filtering portion; 31: candle filter; 32: active carbon filter; 33: first water pump; 34: film filtering portion; 35: second water pump; 40: water tank portion; 41: intermediate water tank; 42: pure water tank; 43: liquid storage tank; 50: heating portion; 60: inlet pipe segment; 70: temperature control portion; 71: refrigerating device; and 72: heating device.

DETAILED DESCRIPTION OF THE EMBODIMENTS

It is noted that embodiments in the application and features in the embodiments may be mutually combined in the case without conflicting. The present disclosure is explained in detail with reference to the drawings in combination with the embodiments below.

It is understood that terms used herein only aim to describe specific implementation manners, and are not intended to limit exemplary implementations of the application. Unless otherwise directed by the context, singular forms of terms used herein are intended to include plural forms. Besides, it is further to be understood that when terms "contain" and/or "include" are used in the description, it is indicated that features, steps, operations, devices, assemblies and/or a combination thereof exist.

It is noted that specification and claims of the disclosure and terms 'first', 'second' and the like in the drawings are intended to distinguish similar objects, and are not necessarily to describe a specific sequence or a precedence order. It is understood that terms used in such a way may be exchanged under appropriate conditions, so that the embodiments of the disclosure described here can be implemented in a sequence other than the sequences graphically shown or described here. In addition, terms 'comprise', 'include' and variations thereof are intended to cover non-exclusive inclusions. For example, processes, methods, systems, products or devices containing a series of steps or units do not need to clearly show those steps or units, and may include other inherent steps or units of these processes, methods, products or devices, which are not clearly shown.

For ease of description, spatial relative terms such as "over", "above", "on an upper surface" and "upper" may be used herein for describing a spatial position relation between a device or feature and other devices or features shown in the drawings. It is understood that the spatial relative terms aim to contain different orientations in usage or operation other than the orientations of the devices described in the drawings. For example, if the devices in the drawings are inverted, devices described as "above other devices or structures" or "over other devices or structures" will be located as "below other devices or structures" or "under other devices or structures". Thus, an exemplary term "above" may include two orientations namely "above" and "below". The device may be located in other different modes (rotated by 90 degrees or located in other orientations), and spatial relative descriptions used herein are correspondingly explained.

Now, the exemplary embodiments according to the disclosure will be described in detail with reference to the drawings. However, the exemplary embodiments may be implemented in multiple different modes, and are not intended to be limited by the described implementation modes herein. It is understood that the implementation modes are provided so that the disclosure is completely and totally disclosed, and the conceptions of the example implementation modes are adequately transmitted to those of ordinarily skill in the art, in the drawings, for clarity, the thicknesses of layers and areas may be enlarged, and the same drawing mark is used for representing the same device, so that their description is omitted.

A mode of adding urea particles to the stirring tank mainly includes two types of addition: spiral conveying addition and vacuum suction addition. Because an addition mode of spiral conveying has the characteristics of large addition amount, continuous addition, and small influence by urea agglomeration, the addition mode of the spiral conveying is extensively applied to production of urea water solution in a large-scale chemical plant. But the addition mode of the spiral conveying has the following defects.

Packaged urea particles need to be poured into a specified hopper firstly, in a practical operation, various unknown impurities may be easily introduced in a process so that solution quality is affected, and labor capacity of a worker is increased.

Along with reduction of the urea particles in the hopper, addition capacity of the urea particles is reduced, finally, if the urea particles attached to the hopper wall cannot be smoothly slid into an activity range of a spiral rod, the urea particles may not be smoothly added to a mixing box, in small-batch production, the urea particles which do not enter the solution mixing box may cause unqualified solution concentration, especially in the small-batch production, this influence is particularly apparent. A special hopper and a spiral rod conveying pipe need to be configured, so that volume is large, and it is not beneficial to the miniaturization and the integration of the whole device.

An addition mode of vacuum suction is just the opposite of the addition mode of the spiral conveying, although the addition mode of the vacuum suction may not perform continuous addition, in the small-batch production of a mini-type device, the addition amount may satisfy using requirements. While the addition mode of the vacuum suction is used for feeding, a worker only needs to open a packaging bag, and insert a material intake pipe into the urea particles so that the addition may be realized, the worker does not need to pour the urea particles from the packaging bag, so the pollution of the urea particles is reduced, and labor intensity of the worker is reduced. In addition, the addition mode of the vacuum suction has less requirements for arrangement of the pipe, and is beneficial to the miniaturization and the integration of the device.

Because the urea particles have the characteristics of easy crystallization by absorbing water, a conventional vacuum material adding device easily blocks a filter screen for separating the urea particles and air.

In combination with FIG. 1 to FIG. 8, according to embodiments of the present disclosure, a material intake device is provided.

Figure 1:
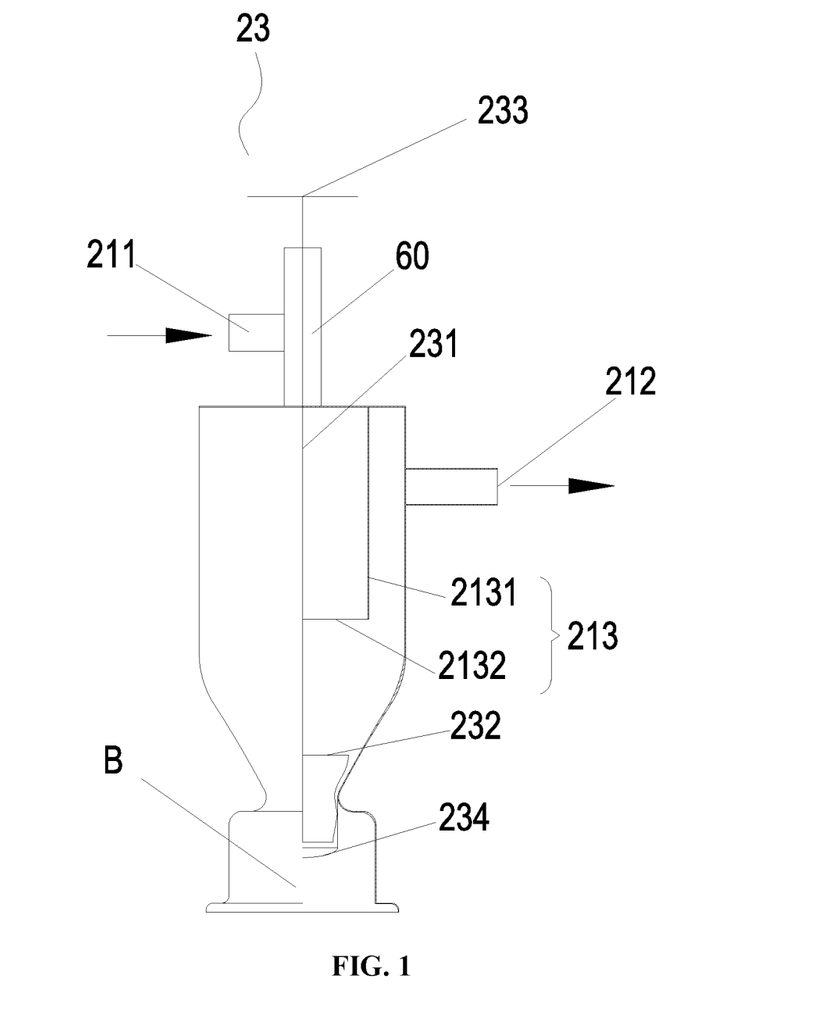
FIG. 1 shows a structure schematic diagram of a first embodiment of a material intake device of a urea preparation machine according to the present disclosure.
Figure 2:
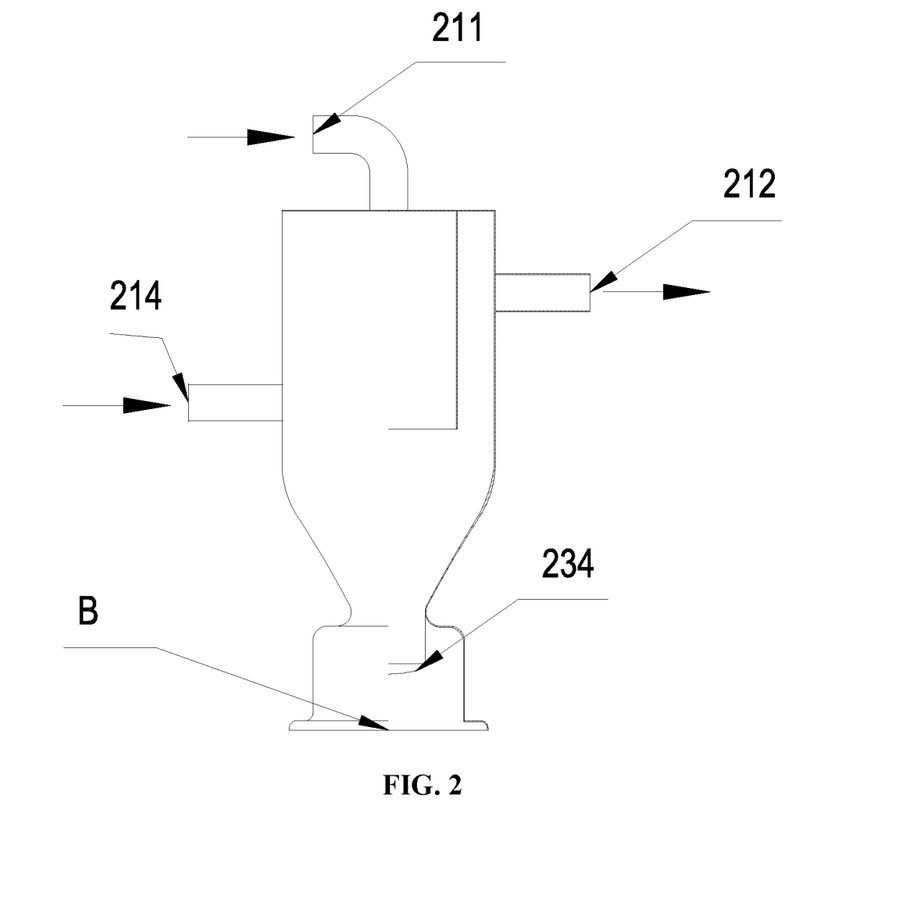
FIG. 2 shows a structure schematic diagram of a second embodiment of the material intake device of the urea preparation machine in FIG. 1.

In an exemplary embodiment, the material intake device includes a housing, an inlet port 211 is provided at a first end of the housing, and an outlet port is provided at a second end of the housing, and the housing is further provided with an exhaust port 212 used for exhausting air in the housing; a separation plate 213 is provided within the housing to isolate the inlet port 211 from the exhaust port 212, an air inlet duct and an exhaust duct are formed respectively between the separation plate 213 and sidewalls of the housing, the exhaust port 212 is communicated with the exhaust duct, and an overflow port connecting the air inlet duct to the exhaust duct is provided between a bottom of the separation plate 213 and the sidewalls of the housing.

In an exemplary embodiment, disposing the separation plate 213 between the inlet port 211 and the exhaust port 212 to separate the inlet port 211 and the exhaust port 212 can effectively prevent urea particles from discharging from the exhaust port 212 resulting in waste thereof when intakes the urea particles from the inlet port 211 and exhausting the air in the material intake device 21, and at the same time can effectively prevent the urea particles from blocking at the material feeding port 211 so as to affect production of urea solutions.

In an exemplary embodiment, the separation plate 213 includes a first plate segment 2131 and a second plate segment 2132. The first plate segment 2131 is provided along a vertical direction, a first end of the first plate segment 2131 is connected to the housing, and the inlet port 211 and the exhaust port 212 are provided at two opposite sides of the first plate segment 2131. The second plate segment 2132 is connected to the second end of the first plate segment 2131 and there is an included angle between the second plate segment 2132 and the second end of the first plate segment 2131, and the second plate segment 2132 is provided away from the exhaust port. The embodiment may effectively prevent the urea particles from blocking the inlet port, and prevent the urea particles from discharging so as to cause resource waste.

In an exemplary embodiment, the included angle between the second plate segment 2132 and the second end of the first plate segment 2131 is a right angle. The embodiment may prevent the urea particles from discharging so as to cause the waste. At the same time, the included angle is set as the right angle, a speed of the urea particles falling into the stirring tank may be effectively buffered, and a lot of the particles are prevented from stacking at the feeding port of the material intake device so as to cause a blocking problem of the feeding port.

Figure 3:
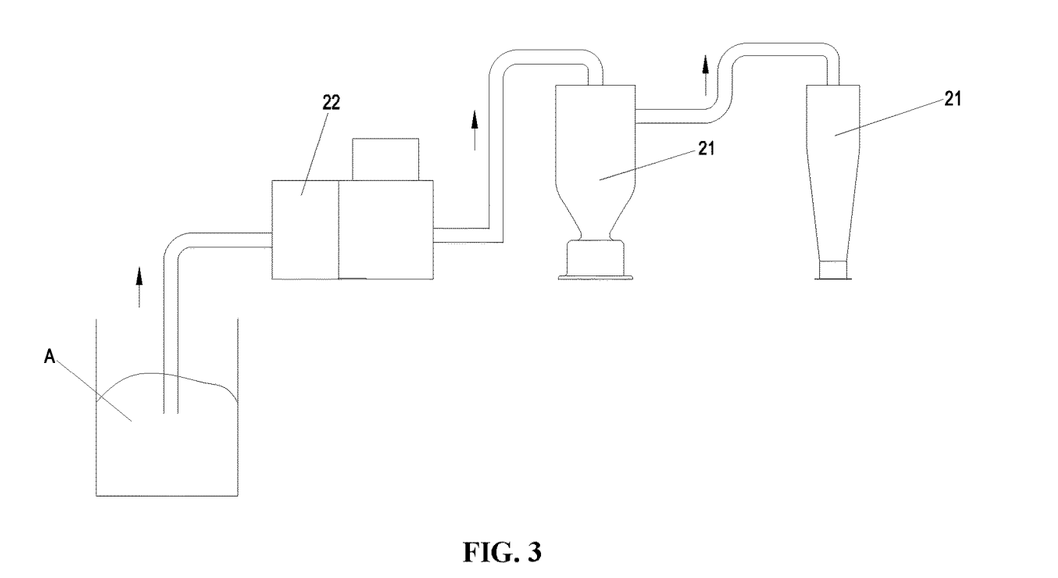
FIG. 3 shows a structure flow diagram of the first embodiment of the material intake device of the urea preparation machine in FIG. 1.
Figure 4:
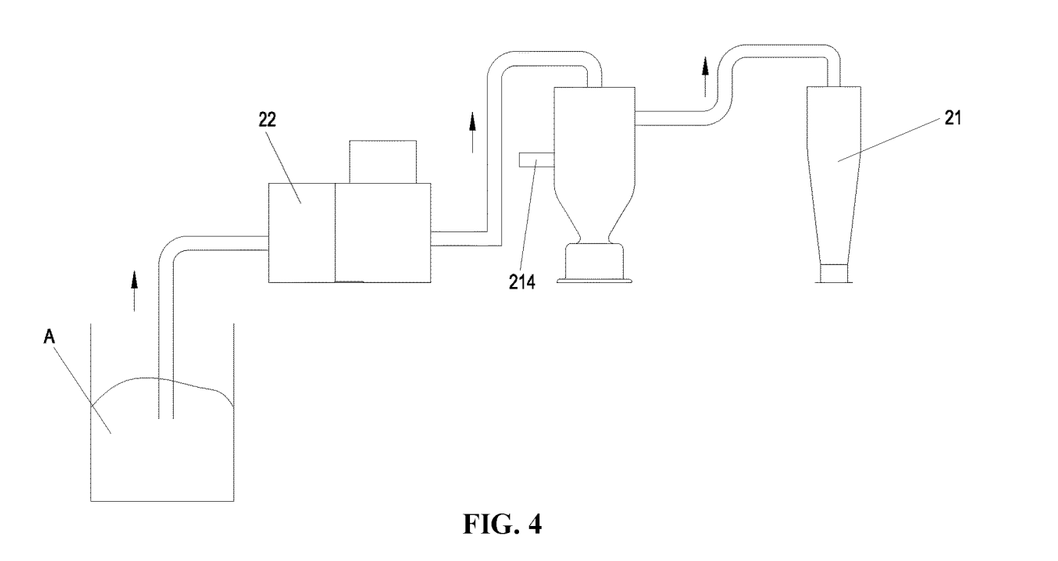
FIG. 4 shows a structure flow diagram of the second embodiment of the material intake device of the urea preparation machine in FIG. 2.

As shown in FIG. 3 and FIG. 4, in an exemplary embodiment, in order to enable the urea particles to enter the stirring tank smoothly, the material intake device includes a suction portion 22. The suction portion 22 is provided with an inlet and an outlet, the outlet is communicated with the inlet port 211, the inlet is used for sucking urea so as to convey the urea into the housing. The inlet is positioned in a container loaded with the urea particles and the outlet is communicated with the inlet port, so when a motor of the suction portion 22 is turned on, the urea particles may be smoothly conveyed into the stirring tank.

In an exemplary embodiment, the material intake device includes a material striking portion 23. The material striking portion 23 is rotatably provided in the housing so as to remove the urea attached to the housing. Such installation of the embodiment may effectively prevent the urea particles from being attached to an inner wall of the housing so as to affect a feeding speed of the urea particles, and such installation of the embodiment may guarantee the stability and reliability of the feeding speed of the material intake device.

In an exemplary embodiment, the material striking portion 23 includes a connecting rod 231 and a rolling plate 232. The connecting rod 231 is rotatably provided at the inlet port 211, a first end of the connecting rod 231 is extended towards an interior of the housing, and a second end of the connecting rod 231 is extended towards an exterior of the housing; the rolling plate 232 is connected to the first end of the connecting rod 231, the rolling plate 232 is extended along the side wall of the housing, the connecting rod 231 drives the rolling plate 232 to rotate along a circumferential direction of the housing. The rolling plate 232 may remove the urea particles attached to the side wall of the housing in a rotation process, and the urea particles are prevented from stacking on the inner wall of the housing so as to affect the stability of feeding the urea particles. In an exemplary embodiment, a tail end of the rolling plate 232 is provided to form a gap with the side wall of the housing.

In an exemplary embodiment, in order to conveniently remove the urea particles attached to the inner wall by an operator, the second end of the connecting rod 231 is provided with a T-shaped handle 233. The handle 233 is held by hands and is rotated so as to achieve a material striking effect.

In an exemplary embodiment, the material striking portion 23 includes a material blocking plate 234. The material blocking plate 234 is movably provided in the housing and positioned below the rolling plate 232. The material blocking plate is provided so that while the suction portion 22 is operated, the material intake device is vacuumized by the suction portion 22, at this moment, the material blocking plate 234 is upwards moved so as to close the outlet positioned above the material blocking plate 234, under an action of the suction portion 22, the urea particles are continuously stacked in the housing, while the suction portion 22 stops working, the material blocking plate 234 is downwards rotated to open the outlet, the urea particles enter the stirring tank at this moment, namely the material blocking plate 234 is repeatedly opened and closed in the intermittent work of the suction portion 22. In addition, the material blocking plate 234 prevents the urea particles positioned below the material blocking plate 234 from reversely sucking to the above housing so as to cause the waste of the urea particles.

In an exemplary embodiment, with reference to FIG. 1, the material intake device includes a inlet pipe segment 60, one end of the inlet pipe segment 60 is communicated with a cavity of the housing, a side wall of the inlet pipe segment 60 is provided with the inlet port 211, the other end of the inlet pipe segment 60 is a free end and is closed, a part of the connecting rod 231 is provided in the inlet pipe segment 60, and the connecting rod 231 and the inlet pipe segment 60 are coaxially provided. Such installation of the embodiment may install the connecting rod 231 on the housing and realize the rotation.

In an exemplary embodiment, in order to clean the interior of the housing in time, the housing is further provided with a water inlet 214. The interior of the housing may be washed by conveying water into the housing through the water inlet 214, the urea particles are prevented from being attached to the inner wall of the housing for a long time so as to corrode the housing, and affect service life of the housing. While the suction portion 22 is located in a working state, the water inlet is located in a closing state, the water inlet is only opened while the water needs to be conveyed into the housing.

As shown in FIG. 3 and FIG. 4, there are a plurality of housings, the inlet port 211 of one housing of the neighboring two housings is communicated with an exhaust port 212 of the other housing in the neighboring two housings. The material outlet of each of the housings is communicated with the cavity of the stirring tank. Through such installation, while a part of the urea particles is discharged from the exhaust duct of the previous housing, the part of the urea particles enter the next housing again, and are conveyed to the material outlet through the air inlet duct in the housing and enter the stirring tank, a second exhaust effect is achieved, similar operations are successively performed. Such installation may effectively convey all of the urea particles from the conveying pipe to the stirring tank for preparing the urea solution, so a utilization ratio of the urea particles is up to one hundred percent and zero waste is achieved.

As shown in FIG. 5 to FIG. 8, some embodiments of the present disclosure provide a urea preparation machine. The urea preparation machine includes a material intake device. The material intake device is the material intake device in the above embodiments. In an exemplary embodiment, the material intake device includes a housing, an inlet port 211 is provided at a first end of the housing, and an outlet port is provided at a second end of the housing, and the housing is further provided with an exhaust port 212 used for exhausting the air in the housing; a separation plate 213 is provided within the housing to isolate the inlet port 211 from the exhaust port 212, an air inlet duct and an exhaust duct are formed respectively between the separation plate 213 and sidewalls of the housing, and the exhaust port 212 is communicated with the exhaust duct; an overflow port communicated with the air inlet duct and the exhaust duct is formed between a bottom of the separation plate 213 and the sidewalls of the housing. Disposing the separation plate 213 between the inlet port 211 and the exhaust port 212 to separate the inlet port 211 and the exhaust port 212 can effectively prevent urea particles from discharging from the exhaust port 212 resulting in waste thereof when intaking the urea particles from the inlet port 211 and exhausting the air in the material intake device 21, and at the same time can effectively prevent the urea particles from blocking at the material feeding port 211 so as to affect production of urea solutions.

Figure 5:
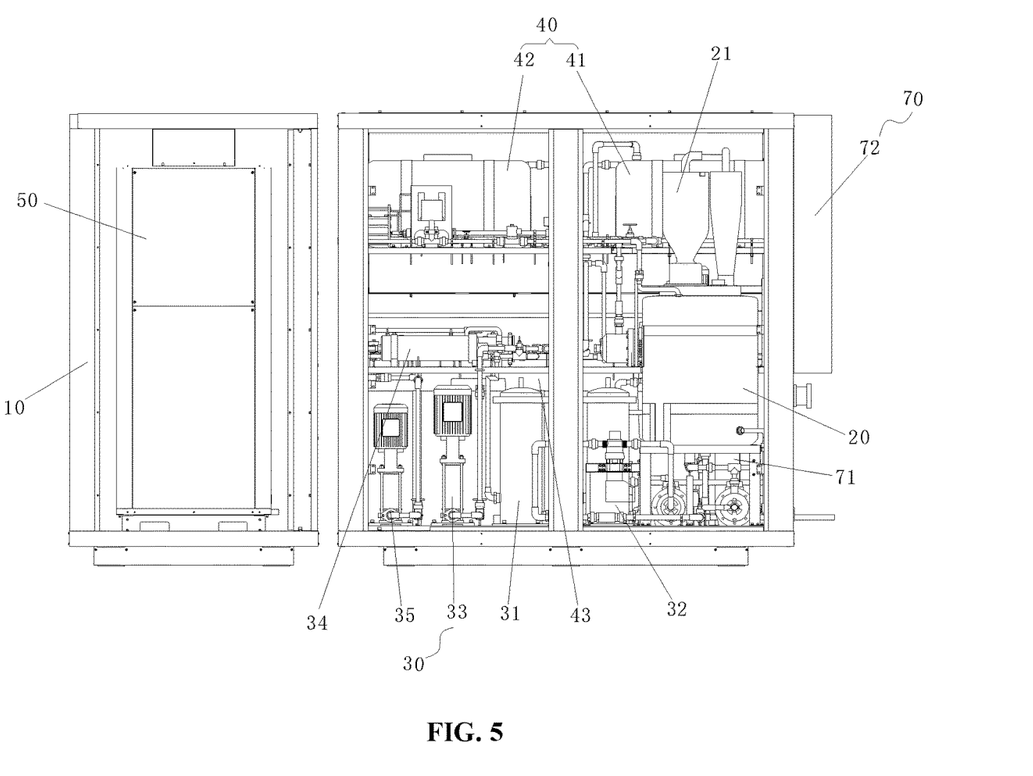
FIG. 5 shows a structure schematic diagram of the urea preparation machine in FIG. 1.
Figure 6:
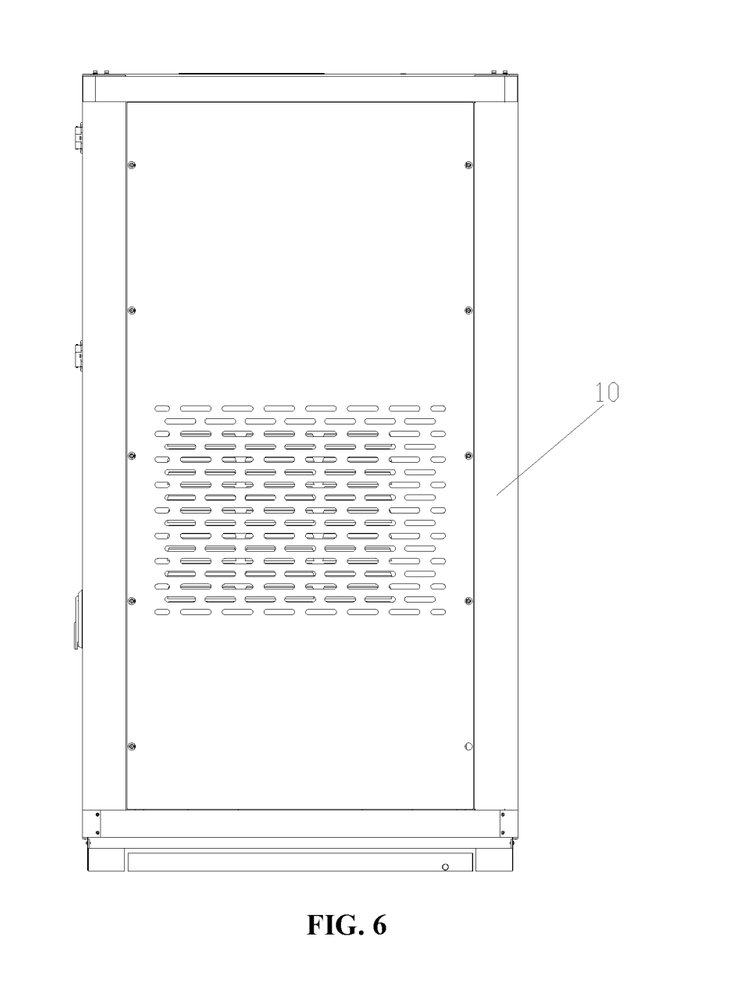
FIG. 6 shows a structure schematic diagram of a first viewing angle of the urea preparation machine in FIG. 5.
Figure 7:
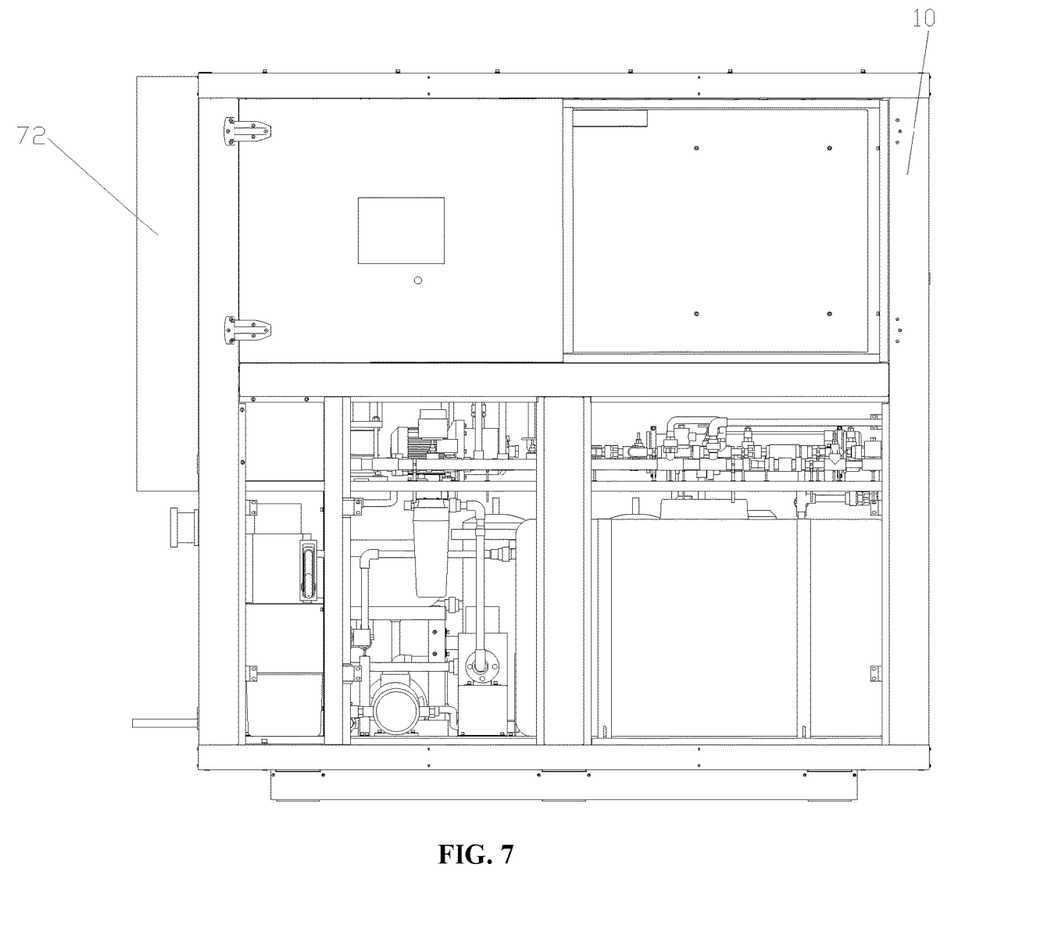
FIG. 7 shows a structure schematic diagram of a second viewing angle of the urea preparation machine in FIG. 5.
Figure 8:
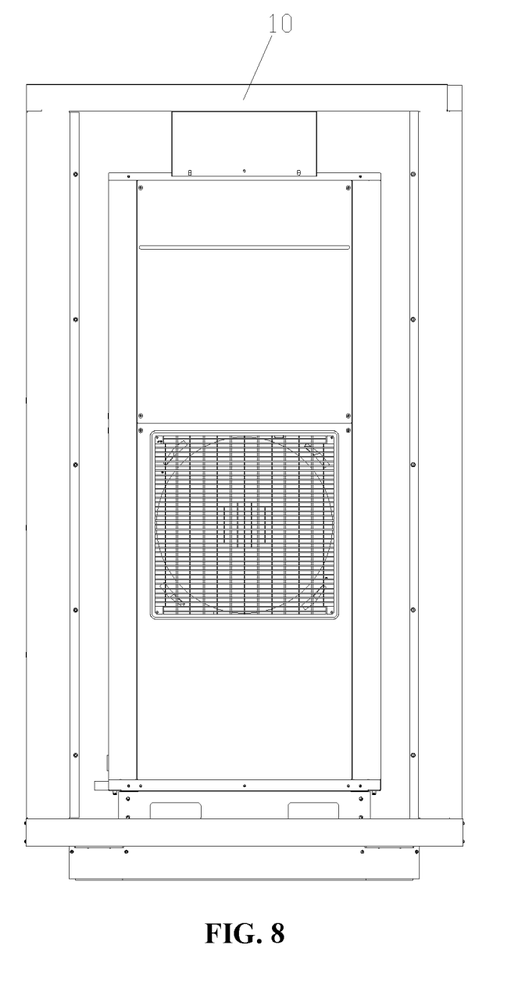
FIG. 8 shows a structure schematic diagram of a third viewing angle of the urea preparation machine in FIG. 5.

In an exemplary embodiment, the urea preparation machine includes a cabinet 10, a stirring tank 20, a filtering portion 30, a water tank portion 40 and a heating portion 50. The stirring tank 20 is provided in the cabinet 10. The filtering portion 30 is provided in the cabinet 10. An inlet of the water tank portion 40 is communicated with an outlet of the filtering portion 30. The heating portion 50 is provided in the cabinet 10. The heating portion 50 is communicated with the outlet of the water tank portion 40. An outlet of the heating portion 50 is communicated with the stirring tank 20.

In the embodiment, the independent heating portion 50 is used for heating water in the water tank portion 40, and the water heated by the heating portion 50 is conveyed to the stirring tank 20 for preparing the urea, such installation of the embodiment is capable of enabling the heating portion 50 to heat the water in the water tank portion 40 in time, effectively improving the efficiency of the urea preparation machine, and satisfying user requirements.

In an exemplary embodiment, the heating portion 50 is provided at one side of at least one of the stirring tank 20, the filtering portion 30 and the water tank portion 40. Such installation of the embodiment can effectively reduce the processing difficulty of the housing of the urea preparation machine, and the layout of the urea preparation machine is more rational and simpler. In an exemplary embodiment, as shown in FIG. 5, the heating portion 50 is provided at one side of the stirring tank 20, the filtering portion 30 and the water tank portion 40.

In an exemplary embodiment, the filtering portion 30 includes a filter. The filter is provided at a bottom of the cabinet 10, a water inlet of the filter is communicated with an external water source, and a water outlet of the filter is communicated with the water tank portion 40. Such installation of the embodiment may effectively filter impurities from external water source, the quality of the urea solution is effectively improved.

In an exemplary embodiment, the filter includes a candle filter 31. A water inlet of the candle filter 31 is communicated with the external water source, and a water outlet of the candle filter 31 is communicated with the water tank portion 40. Such installation of the embodiment may effectively filter small particle fine sand and other impurities in the water source.

In order to further improve the filterability of the filter, in an exemplary embodiment, the filter further includes an active carbon filter 32. A water inlet of the active carbon filter 32 is communicated with the water outlet of the candle filter 31, and a water outlet of the active carbon filter 32 is communicated with the water tank portion 40. Such installation of the embodiment may effective remove low molecular weight organic matters and heavy metals from the water in the candle filter 31.

In an exemplary embodiment, in order to guarantee an enough water pressure in a whole water cycle, the filtering portion 30 further includes a first water pump 33. The first water pump 33 is provided on a pipeline between the stirring tank 20 and the water tank portion 40.

In an exemplary embodiment, the filtering portion 30 includes a film filtering portion 34. The film filtering portion 34 is provided on a pipeline between the stirring tank 20 and the water tank portion 40 and is positioned above the first water pump 33. The embodiment may further achieve the filtering effect to the external water source, the water quality is effectively improved, thereby the quality of the urea solution is improved, and the reliability of the urea preparation machine is increased.

In an exemplary embodiment, the water tank portion 40 includes an intermediate water tank 41. The intermediate water tank 41 is provided above the stirring tank 20, a water inlet of the intermediate water tank 41 is communicated with the water outlet of the filtering portion 30, and a water outlet of the intermediate water tank 41 is communicated with the heating portion 50. The embodiment may store the filtered water in the intermediate water tank, so while a large batch of the urea solution needs to be produced, enough water is prepared for standby.

In an exemplary embodiment, the water tank portion 40 further includes a pure water tank 42. The pure water tank 42 is provided above the filtering portion 30 and parallelly installed with the intermediate water tank 41, a water inlet of the pure water tank 42 is communicated with the water outlet of the intermediate water tank 41, and a water outlet of the pure water tank 42 is communicated with the heating portion 50. The embodiment is capable of enabling the water in the intermediate water tank 41 to be used for preparation while the pure water tank 42 prepares pure water, and conveys the water into the heating portion 50 for heating. A rate of the urea preparation of the urea preparation machine is effectively improved.

In an exemplary embodiment, the water tank portion 40 further includes a liquid storage tank 43. The liquid storage tank 43 is provided on the bottom of the cabinet 10, the first water pump 33 is provided at one side of the liquid storage tank 43, a liquid inlet of the liquid storage tank 43 is communicated with a liquid outlet of the stirring tank 20, and a liquid outlet of the liquid storage tank 43 is communicated with a user end. The liquid storage tank 43 and the first water pump 33 are provided on the bottom of the cabinet 10, through such installation, the first water pump 33 with heavier weight is avoided installing on the liquid storage tank 43 so as to cause an unstable condition that a gravity center of the cabinet of the urea preparation machine is higher. The bottom of the water tank portion 40 is provided with the liquid storage tank 43, so the urea solution prepared in the stirring tank may be stored for future use.

In an exemplary embodiment, the filtering portion 30 includes a second water pump 35. The second water pump 35 is provided on the bottom of the cabinet 10, and the second water pump 35 is provided on a pipeline between the intermediate water tank 41 and the stirring tank 20. The embodiment may guarantee that the pipeline has enough water pressure for conveying a water flow.

In an exemplary embodiment, the heating portion 50 includes a heating water tank. The heating water tank is used for storing and heating water from the water tank portion 40. Such installation is capable of enabling the heating water tank to store the water in a certain heat quantity temperature, and while the urea solution is prepared again, the water in the water tank portion 40 is conveyed to the heating water tank for heating, because the water in a quite high temperature is originally stored in the heating water tank, the water from the water tank portion 40 is mixed with the original water, and the water in the heating water tank may reach the needed water temperature by heating for a short time, and then the water is conveyed to the stirring tank for preparing the urea solution, the heating time of the water needed for preparing the urea solution may be effectively shortened, the applicability and the reliability of the urea solution are improved.

The material intake device 21 in the above embodiment may be further used for the technical field of the urea preparation machine. For example, according to some embodiments of the present disclosure providing a urea preparation machine, the urea preparation machine includes a material intake device 21. The material intake device 21 is provided with a material intake port and a material discharging port. The material discharging port is communicated with a stirring cavity of the stirring tank 20, the material intake port is used for absorbing the urea so as to convey the urea to the stirring cavity. The material intake device is used for feeding the urea particles, and feeding stability and reliability of the urea particles are effectively increased.

The material intake device 21 includes a housing, an inlet port 211 is provided at a first end of the housing, an outlet port is provided at a second end of the housing, the housing is further provided with an exhaust port 212 used for exhausting the air in the housing, and the inlet port 211 forms a material intake port. Such installation of the embodiment effectively increases the feeding stability and reliability of the urea particles.

In an exemplary embodiment, the urea preparation machine includes a cabinet 10 and a temperature control portion 70. The temperature control portion 70 is provided in the cabinet 10, and the temperature control portion 70 is used for controlling a temperature in the cabinet 10 within a preset temperature range.

In the embodiment, the interior of the cabinet of the urea preparation machine is provided with the temperature control portion, and the temperature control portion is capable of effectively controlling the temperature in the cabinet within a certain range, effectively guaranteeing the temperature in the cabinet to be always within a constant temperature range, and guaranteeing the quality of the urea solution stored in the cabinet.

In an exemplary embodiment, the urea preparation machine includes a stirring tank 20 and a water tank portion 40, the stirring tank 20 and the water tank portion 40 are provided in the cabinet 10, and the temperature control portion 70 is used for controlling a temperature of the urea solution in the water tank portion 40 within the preset temperature range. Such installation is capable of effectively keeping a temperature of a water tank installed in the cabinet 10 within a certain temperature range value, and effectively improving the usability of the urea preparation machine and the reliability of preparing the urea solution.

In an exemplary embodiment, the water tank portion 40 includes a liquid storage tank 43. The liquid storage tank 43 is provided on a bottom of the cabinet 10, a liquid inlet of the liquid storage tank 43 is communicated with a liquid outlet of the stirring tank 20, and a liquid outlet of the liquid storage tank 43 is communicated with a user end, and the temperature control portion 70 is used for controlling a temperature in the liquid storage tank 43 so that the temperature of the urea solution in the liquid storage tank 43 is within the preset temperature range. The embodiment is capable of effectively controlling a storage temperature of the urea solution in the liquid storage tank 43. In an exemplary embodiment, a preset temperature is set as t, where t is greater than or equal to 5° C., and is less than or equal to 35° C. Namely, an internal temperature of the cabinet 10 is controlled with the range, so the quality of the urea solution stored in the liquid storage tank 43 may be effectively prevented from being affected because of the excessive high or excessive low temperature.

In an exemplary embodiment, the temperature control portion 70 includes a refrigerating device 71. The refrigerating device 71 is provided on the cabinet 10 and used for reducing the temperature in the cabinet 10. In order to avoid excessive high temperature in the cabinet, the cabinet 10 is provided with the refrigerating device 71 for reducing the internal temperature of the cabinet. The refrigerating device 71 may be an evaporator, or a radiator, such as a fan.

In an exemplary embodiment, in order to prevent excessive low temperature in the cabinet, the temperature control portion 70 further includes a heating device 72. The heating device 72 is provided in the cabinet 10, and the heating device 72 is used for increasing the temperature in the cabinet. Such installation is capable of effectively preventing the urea solution in the liquid storage tank 43 from being reduced because of the excessive low temperature and precipitation. The reliability of the urea preparation machine for preparing the urea solution is effectively improved.

In an exemplary embodiment, the temperature control portion 70 includes a temperature sensor and a controller, the controller controls the temperature in the cabinet through a detecting result of the temperature sensor. Such installation is capable of effectively increasing the controllability of the internal temperature of the cabinet. In addition, the intelligent control of the temperature control in an internal environment of the cabinet 10 is improved, and the sensitivity of controlling the cabinet environment temperature is improved.

In an exemplary embodiment, in order to improve the reliability of a temperature control system, a plurality of heating devices 72 may be provided in the cabinet. The heating device 72 may be an electric heating tube with a heating function or a heat exchange coil with an instant heating function.

In an exemplary embodiment, the cabinet 10 is provided with a door plate structure. The door plate structure is provided with a door plate body. The door plate body is internally provided with a foaming material. Such installation is capable of effectively guaranteeing the stability of the temperature in the cabinet 10, and enabling the cabinet 10 to have a heat-insulating function.

In an exemplary embodiment, the foaming material includes isocyanate and compositional polyether the door plate structure prepared by using the isocyanate and compositional polyether has a stronger heat-insulating effect.

In order to further improve the heat-insulating function of the door plate structure, and avoid air in the cabinet from performing heat exchange with the outside air through the door plate structure, an edge in the door plate body is provided with sponge and foaming rubber, or may be provided with one of the sponge and foaming rubber.

As shown in FIG. 2, in order to clean the interior of the housing in time, the housing is further provided with a water inlet 214. The interior of the housing is washed by conveying water into the housing through the water inlet 214, and the urea particles are prevented from being attached to the inner wall of the housing for a long time so as to corrode the housing, and affect service life of the housing.

In an exemplary embodiment, the suction portion 22 sucks the urea particles from a container (as shown in A in FIG. 3 and FIG. 4) loaded with the urea particles and conveys the urea particles to the material intake device 21 (two material intake devices 21 respectively as shown in FIG. 3 and FIG. 4), and sends the urea particles to the urea stirring tank for preparing the urea solution through a feeding port (as shown in B in FIG. 1 and FIG. 2) of the material intake device 21.

The above are only preferred embodiments of the disclosure, and are not intended to limit the disclosure. As will occur to those skilled in the art, the disclosure is susceptible to various modifications and changes. Any modifications, equivalent replacements, improvements and the like made within the spirit and principle of the disclosure shall fall within the scope of protection of the disclosure.

What is claimed is:

1. A material intake device, comprising:
    a housing, wherein an inlet port is provided at a side of the housing for material intake, and an exhaust port is provided at another side for exhausting air in the housing; and
    a separation plate provided within the housing to isolate the inlet port from the exhaust port, wherein an air inlet duct and an exhaust duct are formed respectively between the separation plate and sidewalls of the housing, the exhaust port communicates with the exhaust duct, the separation plate comprises a first plate segment and a second plate segment, the inlet port and the exhaust port are provided at two opposite sides of the first plate segment, the second plate segment is connected to an end of the first plate segment with an included angle, and an overflow port connecting the air inlet duct to the exhaust duct is provided between the second plate segment of the separation plate and the sidewalls of the housing.

2. The material intake device according to claim 1, wherein the included angle between the second plate segment and the second end of the first plate segment is a right angle.

3. The material intake device according to claim 1, further comprising:
    a suction portion, wherein the suction portion is provided with an inlet and an outlet, the outlet is communicated with the inlet port, and the inlet is used for sucking urea so as to convey urea into the housing.

4. The material intake device according to claim 1, further comprising:
    a material striking portion, wherein the material striking portion is rotatably provided in the housing so as to remove urea attached to the housing.

5. The material intake device according to claim 4, wherein the material striking portion comprises:
    a connecting rod, wherein the connecting rod is rotatably provided at the inlet port, a first end of the connecting rod extends towards an interior of the housing, and a second end of the connecting rod extends towards an exterior of the housing; and
    a rolling plate, wherein the rolling plate is connected with the first end of the connecting rod, the rolling plate extends along the side wall of the housing, and the connecting rod is able to drive the rolling plate to rotate along a circumferential direction of the housing.

6. The material intake device according to claim 5, wherein the material striking portion further comprises:
    a handle, wherein the handle is provided on the second end of the connecting rod.

7. The material intake device according to claim 5, wherein the material striking portion comprises:
    a material blocking plate, wherein the material blocking plate is provided in the housing and positioned below the rolling plate.

8. The material intake device according to claim 5, further comprising:
    an inlet pipe segment, wherein one end of the inlet pipe segment is communicated with a cavity of the housing, a side wall of the inlet pipe segment is provided with the inlet port, the other end of the inlet pipe segment is a free end and is closed, a part of the connecting rod is positioned in the inlet pipe segment—and the connecting rod and the inlet pipe segment are coaxially provided.

9. The material intake device according to claim 1, wherein the housing is further provided with a water inlet.

10. A material intake device, comprising:
    a housing, wherein an inlet port is provided at a first end of the housing, and an outlet port is provided at a second end of the housing, and the housing is further provided with an exhaust port used for exhausting air in the housing; and a separation plate, wherein the separation plate is provided within the housing to isolate the inlet port from the exhaust port, an air inlet duct and an exhaust duct are formed respectively between the separation plate and sidewalls of the housing, the exhaust port is communicated with the exhaust duct, and an overflow port connecting the air inlet duct to the exhaust duct is provided between a bottom of the separation plate and the sidewalls of the housing, wherein the separation plate comprises:

a first plate segment, wherein the first plate segment is provided along a vertical direction, a first end of the first plate segment is connected to the housing, and the inlet port and the exhaust port are provided at two opposite sides of the first plate segment; and a second plate segment, wherein the second plate segment is connected to a second end of the first plate segment with an included angle, and the second plate segment is provided away from the exhaust port.

11. A urea preparation machine, comprising the material intake device according to claim 10.

12. The machine according to claim 11, wherein the material intake device comprises:

a suction portion, wherein the suction portion is provided with an inlet and an outlet, the outlet is communicated with the inlet port, and the inlet is used for sucking urea so as to convey urea into the housing.

13. The machine according to claim 11, wherein the material intake device comprises:

a material striking portion rotatably provided in the housing for removing urea attached to the housing, wherein the material striking portion comprises:

a connecting rod rotatably provided at the inlet port, wherein a first end of the connecting rod extends towards an interior of the housing, and a second end of the connecting rod extends towards an exterior of the housing; and a rolling plate connected with the first end of the connecting rod, wherein the rolling plate extends along the side wall of the housing, and the connecting rod is able to drive the rolling plate to rotate along a circumferential direction of the housing.

14. The machine according to claim 13, wherein the material striking portion further comprises:

a handle provided on the second end of the connecting rod;

a material blocking plate provided in the housing and positioned below the rolling plate; and/or an inlet pipe segment, wherein one end of the inlet pipe segment is communicated with a cavity of the housing, a side wall of the inlet pipe segment is provided with the inlet port, the other end of the inlet pipe segment is a free end and is closed, a part of the connecting rod is positioned in the inlet pipe segment—and the connecting rod and the inlet pipe segment are coaxially provided.

15. The machine according to claim 11, wherein the housing is further provided with a water inlet.

16. A urea preparation machine, comprising:

a material intake device comprising:

a housing, wherein an inlet port is provided at a side of the housing for material intake, and an exhaust port is provided at another side for exhausting air in the housing; and a separation plate provided within the housing to isolate the inlet port from the exhaust port, wherein an air inlet duct and an exhaust duct are formed respectively between the separation plate and sidewalls of the housing, the exhaust port communicates with the exhaust duct, the separation plate comprises a first plate segment and a second plate segment, the inlet port and the exhaust port are provided at two opposite sides of the first plate segment, the second plate segment is connected to an end of the first plate segment with an included angle, and an overflow port connecting the air inlet duct to the exhaust duct is provided between the second plate segment of the separation plate and the sidewalls of the housing.

17. The machine according to claim 16, wherein the material intake device comprises:

a suction portion, wherein the suction portion is provided with an inlet and an outlet, the outlet is communicated with the inlet port, and the inlet is used for sucking urea so as to convey urea into the housing.

18. The machine according to claim 16, wherein the material intake device comprises:

a material striking portion rotatably provided in the housing for removing urea attached to the housing, wherein the material striking portion comprises:

a connecting rod rotatably provided at the inlet port, wherein a first end of the connecting rod extends towards an interior of the housing, and a second end of the connecting rod extends towards an exterior of the housing; and a rolling plate connected with the first end of the connecting rod, wherein the rolling plate extends along the side wall of the housing, and the connecting rod is able to drive the rolling plate to rotate along a circumferential direction of the housing.

19. The machine according to claim 18, wherein the material striking portion further comprises:

a handle provided on the second end of the connecting rod;

a material blocking plate provided in the housing and positioned below the rolling plate; and/or an inlet pipe segment, wherein one end of the inlet pipe segment is communicated with a cavity of the housing, a side wall of the inlet pipe segment is provided with the inlet port, the other end of the inlet pipe segment is a free end and is closed, a part of the connecting rod is positioned in the inlet pipe segment—and the connecting rod and the inlet pipe segment are coaxially provided.

20. The machine according to claim 16, wherein the housing is further provided with a water inlet.

* * * * *